United States Patent [19]

Brodeur et al.

[11] Patent Number: 5,601,820
[45] Date of Patent: Feb. 11, 1997

[54] COMPOSITIONS AND METHODS OF MAKING AND USING HUMAN FULL LENGTH TRK-B

[75] Inventors: Garrett M. Brodeur; Akira Nakagawara, both of Philadelphia, Pa.

[73] Assignee: Children's Hospital of Philadelphia, Philadelphia, Pa.

[21] Appl. No.: 271,454

[22] Filed: Jul. 7, 1994

[51] Int. Cl.[6] .......................... A61K 39/395; C12Q 1/68; C12P 19/34; C07H 21/02
[52] U.S. Cl. .......................... 424/138.1; 435/6; 435/91.2; 536/23.1; 536/24.3
[58] Field of Search .................. 435/6, 91.2; 536/23.1, 536/24.3–24.33; 424/138.1

[56] References Cited

U.S. PATENT DOCUMENTS

| | | | |
|---|---|---|---|
| 4,736,866 | 4/1988 | Leder | 800/1 |
| 4,873,191 | 10/1989 | Wagner | 435/172.3 |
| 5,231,001 | 7/1993 | Kaplan et al. | 435/7.1 |

OTHER PUBLICATIONS

Allan et al. Neuroscience 60: 825–834 1994.
Middlemass, Molecular and Cellular Biology 11: 143–153 1991.
Ausubel et al, In a Compendium of Methods from Current Protocols in Molecular Biology, Harvard Med. School, MA pp. 15–13 to 15–20 1993.
Innis and Gelfand, in PCR Protocols, Academic Press, San Diego, CA., pp. 15–16 1990.
Manak and Keller, in DNA Probes, MacMillan Publishers, N.Y. 1993.
Ehrhard, P. et al., "Expression of Low-affinity NGF Receptor and trkB mRNA in Human SH-SY5Y Neuroblastoma Cells", FEBS 1993, 330(3), 287–292.
Merlio, J.-P. et al., "Increased Production of the TrkB Protein Tyrosine Kinase Receptor after Brain Insults", Neuron 1993, 10, 151–164.
Nakagawara, A. et al., "Expression and Function of TRK-B and BDNF in Human Neuroblastomas", Molecular and Cellular Biology 1994, 14(1), 759–767.
Klein et al., "The trkB Tyrosine Protein Kinase Gene Codes for a Second Neurogenic Receptor that Lacks the Ctalytic Kinase Domain", Cell 61: 647–656 (1990).
Klein et al., "trkB, a Novel Tyrosine Protein Kinase Receptor Expressed During Mouse Neural Development", EMBO Journal 8: 3701–3709 (1989).
Loose-Mitchell, "Antisense Nucleic Acids as a Potential Class of Pharmaceutical Agents", TIPS 9: 45–47 (1988).
Marcus-Sekura, "Techniques for Using Antisense Oligodeoxyribonucleotides to Study Gene Expression", Anal. Biochemistry 172: 289–295 (1988).
Middlemas et al., "trkB, a Neural Receptor Protein-Tyrosine Kinase: Evidence for a Full-Length and Two Truncated Receptors", Molecular and Cellular Biology 11: 143–153 (1991).
Snider, W. D., "Functions of the Neurotrophins During Nervous System Development: What the Knockouts are Teaching Us", Cell 77: 627–638 (1994).

(List continued on next page.)

Primary Examiner—W. Gary Jones
Assistant Examiner—Dianne Rees
Attorney, Agent, or Firm—Woodcock Washburn Kurtz Mackiewicz & Norris

[57] ABSTRACT

The amino acid sequence of the full length version of the human neurotrophic factor receptor TRK B and a nucleotide sequence encoding it are disclosed. Transformed host cells and transgenic animals containing nucleic acid molecules encoding full length human TRK-B are disclosed. Probes, primers and antisense molecules identical and complementary to the nucleotide sequence that encodes full length human TRK-B, particularly the intracellular portion of the receptor are disclosed. Monoclonal antibodies that bind to the full length human TRK-B protein are disclosed. Methods of using and kits which include probes, primers, antisense molecules and monoclonal antibodies are disclosed.

22 Claims, 2 Drawing Sheets

OTHER PUBLICATIONS

Stein, C. A. & J. S. Cohen, "Oligodeoxynucleotides as Inhibitors of Gene Expression: A Review", *Cancer Research* 48: 2659–2668 (1988).

Van der Krol, J. N. Mol, & A. R. Stuitje, "Modulation of Eukaryotic Gene Expression by Complementary RNA or DNA Sequences", *BioTechniques* 6: 958–973 (1988).

Walder, J., "Antisense DNA and RNA: Progress and Prospects", *Genes & Development* 2: 502–504 (1988).

Zon, "Oligonucleotide Analogues as Potential Chemotherapeutic Agents", *Pharmaceutical Research* 5: 539–549 (1988).

Zon, "Synthesis of Backbone–Modified DNA Analogues for Biological Applications", *Journal of Protein Chemistry* 6:131–145 (1987).

SEQ ID NO:1

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 3707 base pairs
        ( B ) TYPE: nucleic acid
        ( C ) STRANDEDNESS: double
        ( D ) TOPOLOGY: both ( i i ) MOLECULE TYPE: cDNA ( x i ) SEQUENCE DESCRIPTION: SEQ ID NO:1:

```
CCCCCATTCG  CATCTAACAA  GGAATCTGCG  CCCCAGAGAG  TCCCGGACGC  CGCCGGTCGG     60

TGCCCGGCGC  GCCGGGCCAT  GCAGCGACGG  CCGCCGCGGA  GCTCCGAGCA  GCGGTAGCGC    120

CCCCCTGTAA  AGCGGTTCGC  TATGCCGGGA  CCACTGTGAA  CCCTGCCGCC  TGCCGGAACA    180

CTCTTCGCTC  CGGACCAGCT  CAGCCTCTGA  TAAGCTGGAC  TCGGCACGCC  CGCAACAAGC    240

ACCGAGGAGT  TAAGAGAGCC  GCAAGCGCAG  GGAAGGCCTC  CCCGCACGGG  TGGGGGAAAG    300

CGGCCGGTGC  AGCGCGGGGA  CAGGCACTCG  GGCTGGCACT  GGCTGCTAGG  GATGTCGTCC    360

TGGATAAGGT  GGCATGGACC  CGCCATGGCG  CGGCTCTGGG  GCTTCTGCTG  GCTGGTTGTG    420

GGCTTCTGGA  GGGCCGCTTT  CGCCTGTCCC  ACGTCCTGCA  AATGCAGTGC  CTCTCGGATC    480

TGGTGCAGCG  ACCCTTCTCC  TGGCATCGTG  GCATTTCCGA  GATTGGAGCC  TAACAGTGTA    540

GATCCTGAGA  ACATCACCGA  AATTTTCATC  GCAAACCAGA  AAAGGTTAGA  AATCATCAAC    600

GAAGATGATG  TTGAAGCTTA  TGTGGGACTG  AGAAATCTGA  CAATTGTGGA  TTCTGGATTA    660

AAATTTGTGG  CTCATAAAGC  ATTTCTGAAA  AACAGCAACC  TGCAGCACAT  CAATTTTACC    720

CGAAACAAAC  TGACGAGTTT  GTCTAGGAAA  CATTTCCGTC  ACCTTGACTT  GTCTGAACTG    780

ATCCTGGTGG  GCAATCCATT  TACATGCTCC  TGTGACATTA  TGTGGATCAA  GACTCTCCAA    840
```

-continued

| | | | | | |
|---|---|---|---|---|---|
| GAGGCTAAAT | CCAGTCCAGA | CACTCAGGAT | TTGTACTGCC | TGAATGAAAG | CAGCAAGAAT | 900 |
| ATTCCCCTGG | CAAACCTGCA | GATACCCAAT | TGTGGTTTGC | CATCTGCAAA | TCTGGCCGCA | 960 |
| CCTAACCTCA | CTGTGGAGGA | AGGAAAGTCT | ATCACATTAT | CCTGTAGTGT | GGCAGGTGAT | 1020 |
| CCGGTTCCTA | ATATGTATTG | GGATGTTGGT | AACCTGGTTT | CCAAACATAT | GAATGAAACA | 1080 |
| AGCCACACAC | AGGGCTCCTT | AAGGATAACT | AACATTTCAT | CCGATGACAG | TGGGAAGCAG | 1140 |
| ATCTCTTGTG | TGGCGGAAAA | TCTTGTAGGA | GAAGATCAAG | ATTCTGTCAA | CCTCACTGTG | 1200 |
| CATTTTGCAC | CAACTATCAC | ATTTCTCGAA | TCTCCAACCT | CAGACCACCA | CTGGTGCATT | 1260 |
| CCATTCACTG | TGAAAGGCAA | CCCCAAACCA | GCGCTTCAGT | GGTTCTATAA | CGGGGCAATA | 1320 |
| TTGAATGAGT | CCAAATACAT | CTGTACTAAA | ATACATGTTA | CCAATCACAC | GGAGTACCAC | 1380 |
| GGCTGCCTCC | AGCTGGATAA | TCCCACTCAC | ATGAACAATG | GGACTACAC | TCTAATAGCC | 1440 |
| AAGAATGAGT | ATGGGAAGGA | TGAGAAACAG | ATTTCTGCTC | ACTTCATGGG | CTGGCCTGGA | 1500 |
| ATTGACGATG | GTGCAAACCC | AAATTATCCT | GATGTAATTT | ATGAAGATTA | TGGAACTGCA | 1560 |
| GCGAATGACA | TCGGGGACAC | CACGAACAGA | AGTAATGAAA | TCCCTTCCAC | AGACGTCACT | 1620 |
| GATAAAACCG | GTCGGGAACA | TCTCTCGGTC | TATGCTGTGG | TGGTGATTGC | GTCTGTGGTG | 1680 |
| GGATTTTGCC | TTTTGGTAAT | GCTGTTTCTG | CTTAAGTTGG | CAAGACACTC | CAAGTTTGGC | 1740 |
| ATGAAGGCC | CAGCCTCCGT | TATCAGCAAT | GATGATGACT | CTGCCAGCCC | ACTCCATCAC | 1800 |
| ATCTCCAATG | GGAGTAACAC | TCCATCTTCT | TCGGAAGGTG | GCCCAGATGC | TGTCATTATT | 1860 |
| GGAATGACCA | AGATCCCTGT | CATTGAAAAT | CCCCAGTACT | TGGCATCAC | CAACAGTCAG | 1920 |
| CTCAAGCCAG | ACACATTTGT | TCAGCACATC | AAGCGACATA | ACATTGTTCT | GAAAAGGGAG | 1980 |
| CTAGGCGAAG | GAGCCTTTGG | AAAAGTGTTC | CTAGCTGAAT | GCTATAACCT | CTGTCCTGAG | 2040 |
| CAGGACAAGA | TCTTGGTGGC | AGTGAAGACC | CTGAAGGATG | CCAGTGACAA | TGCACGCAAG | 2100 |
| GACTTCCACC | GTGAGGCCGA | GCTCCTGACC | AACCTCCAGC | ATGAGCACAT | CGTCAAGTTC | 2160 |
| TATGGCGTCT | GCGTGGAGGG | CGACCCCCTC | ATCATGGTCT | TTGAGTACAT | GAAGCATGGG | 2220 |
| GACCTCAACA | AGTTCCTCAG | GGCACACGGC | CCTGATGCCG | TGCTGATGGC | TGAGGGCAAC | 2280 |
| CCGCCCACGG | AACTGACGCA | GTCGCAGATG | CTGCATATAG | CCCAGCAGAT | CGCCGCGGGC | 2340 |
| ATGGTCTACC | TGGCGTCCCA | GCACTTCGTG | CACCGCGATT | TGGCCACCAG | GAACTGCCTG | 2400 |
| GTCGGGGAGA | ACTTGCTGGT | GAAAATCGGG | GACTTTGGGA | TGTCCCGGGA | CGTGTACAGC | 2460 |
| ACTGACTACT | ACAGGGTCGG | TGGCCACACA | ATGCTGCCCA | TTCGCTGGAT | GCCTCCAGAG | 2520 |
| AGCATCATGT | ACAGGAAATT | CACGACGGAA | AGCGACGTCT | GGAGCCTGGG | GGTCGTGTTG | 2580 |
| TGGGAGATTT | TCACCTATGG | CAAACAGCCC | TGGTACCAGC | TGTCAAACAA | TGAGGTGATA | 2640 |
| GAGTGTATCA | CTCAGGGCCG | AGTCCTGCAG | CGACCCCGCA | CGTGCCCCCA | GGAGGTGTAT | 2700 |
| GAGCTGATGC | TGGGGTGCTG | GCAGCGAGAG | CCCCACATGA | GGAAGAACAT | CAAGGGCATC | 2760 |
| CATACCCTCC | TTCAGAACTT | GGCCAAGGCA | TCTCCGGTCT | ACCTGGACAT | TCTAGGCTAG | 2820 |
| GGCCCTTTTC | CCCAGACCGA | TCCTTCCCAA | CGTACTCCTC | AGACGGGCTG | AGAGGATGAA | 2880 |
| CATCTTTTAA | CTGCCGCTGG | AGGCCACCAA | GCTGCTCTCC | TTCACTCTGA | CAGTATTAAC | 2940 |
| ATCAAAGACT | CCGAGAAGCT | CTCGAGGGAA | GCAGTGTGTA | CTTCTTCATC | CATAGACACA | 3000 |
| GTATTGACTT | CTTTTGGCA | TTATCTCTTT | CTCTCTTTCC | ATCTCCCTTG | GTTGTTCCTT | 3060 |
| TTTCTTTTTT | TAAATTTTCT | TTTTCTTCTT | TTTTTCGTC | TTCCCTGCTT | CACGATTCTT | 3120 |
| ACCCTTTCTT | TTGAATCAAT | CTGGCTTCTG | CATTACTATT | AACTCTGCAT | AGACAAGGC | 3180 |
| CTTAACAAAC | GTAATTTGTT | ATATCAGCAG | ACACTCCAGT | TTGCCCACCA | CAACTAACAA | 3240 |

| | | | | | | | |
|---|---|---|---|---|---|---|---|
| TGCCTTGTTG | TATTCCTGCC | TTTGATGTGG | ATGAAAAAAA | GGGAAAACAA | ATATTTCACT | | 3300 |
| TAAACTTTGT | CACTTCTGCT | GTACAGATAT | CGAGAGTTTC | TATGGATTCA | CTTCTATTTA | | 3360 |
| TTTATTATTA | TTACTGTTCT | TATTGTTTTT | GGATGGCTTA | AGCCTGTGTA | TAAAAAAGAA | | 3420 |
| AACTTGTGTT | CAATCTGTGA | AGCCTTTATC | TATGGGAGAT | TAAAACCAGA | GAGAAAGAAG | | 3480 |
| ATTTATTATG | AACCGCAATA | TGGGAGGAAC | AAAGACAACC | ACTGGGATCA | GCTGGTGTCA | | 3540 |
| GTCCCTACTT | AGGAAATACT | CAGCAACTGT | TAGCTGGGAA | GAATGTATTC | GGCACCTTCC | | 3600 |
| CCTGAGGACC | TTTCTGAGGA | GTAAAAAGAC | TACTGGCCTC | TGTGCCATGG | ATGATTCTTT | | 3660 |
| TCCCATCACC | AGAAATGATA | GCGTGCAGTA | GAGAGCAAAG | ATGGCTT | | | 3707 |

COMPOSITIONS AND METHODS OF MAKING AND USING HUMAN FULL LENGTH TRK-B

FIELD OF THE INVENTION

The present invention relates to the full length version of the human neurotrophic factor receptor TRK-B, (full length human TRK-B), nucleic acid molecules that comprise a nucleotide sequence which encodes a full length version of human TRK-B and fragments thereof and to methods of making and using a full length human TRK-B including mutated forms and antibodies that bind to full length human TRK-B.

BACKGROUND OF THE INVENTION

Developing neurons require trophic factors for survival, growth and differentiation. Nerve growth factor (NGF) was first discovered as a neurotrophic factor that supports the development and maintenance of peripheral sympathetic and neural crest-derived sensory neurons. NGF is a member of a family of proteins that includes brain-derived neurotrophic factor (BDNF), neurotrophin-3 (NT-3) and NT-4/5. Despite the high sequence homology, the developmental and physiological functions of each factor appear to be different.

Three receptors for the neurotrophic factors of the NGF family are known, and they also form a gene family encoding protein tyrosine kinases. TRK-A encodes a receptor for NGF but also binds NT-3 and NT-4/5. TRK-B encodes a receptor for BDNF but also binds NT-3 and NT-4/5. TRK-C encodes a receptor for Nt-3.

TRK-B has two isoforms, a full length version which has an intracellular domain encoded by the 3' portion of the gene sequence and a truncated version which has essentially no intracellular domain. The intracellular domain of the full length TRK-B is responsible for the receptor's tyrosine kinase activity which is linked to BDNF binding to the receptor. The truncated version, lacking an intracellular domain, does not possess tyrosine kinase activity. The amino acid and nucleotide sequences of rat and mouse TRK-B are known. The amino acid and nucleotide sequences of human truncated TRK-B are known while those of the full length version are heretofore unknown.

There is considerable interest in the role of the TRK family of neurotrophin receptors in regulating growth and differentiation in normal and neoplastic nerve cells. A neuroblastoma is a common pediatric tumor derived from the neural crest. It has been observed that neuroblastoma cells expressing TRK-A can differentiate in response to NGF in culture. The most favorable clinical outcomes are found in patients suffering from neuroblastomas that express high levels of TRK-A transcripts. In contrast, aggressive neuroblastomas, especially those with N-myc amplification, express little or no detectable TRK-A mRNA, and many cell lines have a defective NGF receptor signaling pathway. Little is known about the expression or function of TRK-B in these tumors. TRK-B encodes a tyrosine kinase that binds to brain-derived neurotrophic factor (BDNF), as well as neurotrophin-3 (NT-3) and NT-4/5. These results suggest that the biology of neuroblastomas is closely correlated with the developmental stages of the neurons from which the tumors originate, so neuroblastomas may be regulated in part by neurotrophic factors.

In view of the observation that some neuroblastomas present favorable outcomes in response to therapeutic intervention while others are more aggressive behavior and associated with less favorable prognoses and poor outcomes, it is clinically important to distinguish aggressive forms of neuroblastoma from other, less aggressive neuroblastomas. The course of action to be taken in a patient exhibiting neuroblastoma is in part dependent on whether the neuroblastoma is an aggressive form or not because aggressive forms require a more aggressive treatment regimen. Patients suffering from aggressive neuroblastomas must be treated with a relatively potent and specific chemotherapy regimen and surgery may be more appropriate than in those with the type associated with more favorable outcomes. Because the determination of whether a tumor is aggressive or not suggests the prognosis and what course of treatment is warranted, it is crucial to be able to identify whether or not a tumor is an aggressive neuroblastoma in a fast, efficient and reliable manner.

Currently, neuroblastoma may be tested to determine whether or not it possess amplified levels of N-myc. Amplified levels of N-myc indicate an aggressive form of neuroblastoma. The levels of N-myc are evaluated as an indication of aggressive neuroblastoma.

There remains a need for methods of screening neuroblastoma for indications of whether or not it is an aggressive form. Such a method may be used as an alternative to or in concert with the current test to detect levels of N-myc. There remains a need for methods of screening neuroblastoma for indications of whether or not it is an aggressive form by detecting the presence or absence of a marker or target without the need to quantify or determine relative amounts present.

There is a need for the amino acid and nucleotide sequences of human full length TRK-B. The is a need for isolated nucleic acid molecules that encode human full length TRK-B which can be used to transform cells that can then express the human full length TRK-B. There is a need for probes and primers which hybridize to portion of the nucleotide sequences of nucleic acid molecules that encode the human full length TRK-B but not the truncated form. There is a need for antibodies that specifically bind to an epitope on the intracellular domain of human full length TRK-B that is not present in the truncated form.

SUMMARY OF THE INVENTION

The present invention relates to an isolated and pure nucleic acid molecule that encodes full length human TRK-B protein.

The present invention relates to a recombinant vector that comprises a nucleotide sequence that encodes full length human TRK-B protein.

The present invention relates to a recombinant expression vector that comprises a nucleotide sequence that encodes full length human TRK-B protein.

The present invention relates to a transformed host cell that comprises a recombinant expression vector that includes a nucleotide sequence that encodes full length human TRK-B protein.

The present invention relates to isolated and pure nucleic acid molecules that consist of 5–200 nucleotides and that comprise a nucleotide sequence of at least 5 nucleotides which are identical or complementary to at least a fragment of unique nucleotide sequences of full length human TRK-B.

The present invention relates to pharmaceutical compositions that comprise isolated nucleic acid molecules that consist of 5–200 nucleotides and that comprise a nucleotide sequence of at least 5 nucleotides which are identical or complementary to at least a fragment of unique nucleotide sequences of full length human TRK-B.

The present invention relates to essentially pure and isolated full length human TRK-B protein.

The present invention relates to monoclonal antibodies which specifically binds to an epitope on the intracellular domain of full length human TRK-B protein.

The present invention relates to pharmaceutical compositions that comprises monoclonal antibodies which specifically binds to an epitope on the intracellular domain of full length human TRK-B protein.

The present invention relates to a method of determining whether a human neuroblastoma cell expresses full length human TRK-B which comprises determining whether antibodies specific for an epitope on the intracellular domain of full length human TRK-B bind to any proteins in neuroblastoma cells being tested.

The present invention relates to a kit for determining whether a human neuroblastoma cell expresses full length human TRK-B which comprises a container that includes monoclonal antibodies that specifically binds to an epitope on the intracellular domain of full length human TRK-B and a container that includes a protein to which the antibodies bind.

The present invention relates to a method of determining whether a human neuroblastoma cell expresses full length human TRK-B which comprises determining whether PCR fragments are generated from RNA or cDNA from neuroblastoma cells being tested using a set of primers which include at least one that comprises a nucleotide sequence identical or complementary to at least a fragment of the unique nucleotide sequence of full length human TRK-B having at least 5 nucleotides.

The present invention relates to a set of PCR primers which include at least one primer that comprises a nucleotide sequence identical or complementary to at least a fragment of the unique nucleotide sequence of full length human TRK-B having at least 5 nucleotides.

The present invention relates to a kit for determining whether a human neuroblastoma cell expresses full length human TRK-B protein comprising a container that includes a set of PCR primers which include at least one primer that comprises a nucleotide sequence identical or complementary to at least a fragment of the unique nucleotide sequence of full length human TRK-B having at least 5 nucleotides and a container that includes a nucleic acid molecule having the same size as that which would be generated by the primers in the presence of a nucleic acid molecule having SEQ ID NO: 1.

The present invention relates to a method of determining whether a human neuroblastoma cell expresses full length human TRK-B which comprises determining whether oligonucleotide probes, which include a nucleotide sequence identical or complementary to at least a fragment of the unique nucleotide sequence of full length human TRK-B having at least 5 nucleotides, hybridize to RNA or cDNA from neuroblastoma cells being tested.

The present invention relates to a kit for determining whether a human neuroblastoma cell expresses full length human protein comprising a first container that includes an oligonucleotide probe which has a nucleotide sequence identical or complementary to at least a fragment of the unique nucleotide sequence of full length human TRK-B having at least 5 nucleotides and a second container that includes a nucleic acid molecule has a nucleotide sequence that is complementary to the nucleotide sequence of the nucleic acid molecule in the first container.

DETAILED DESCRIPTION OF THE INVENTION

Figure 1:
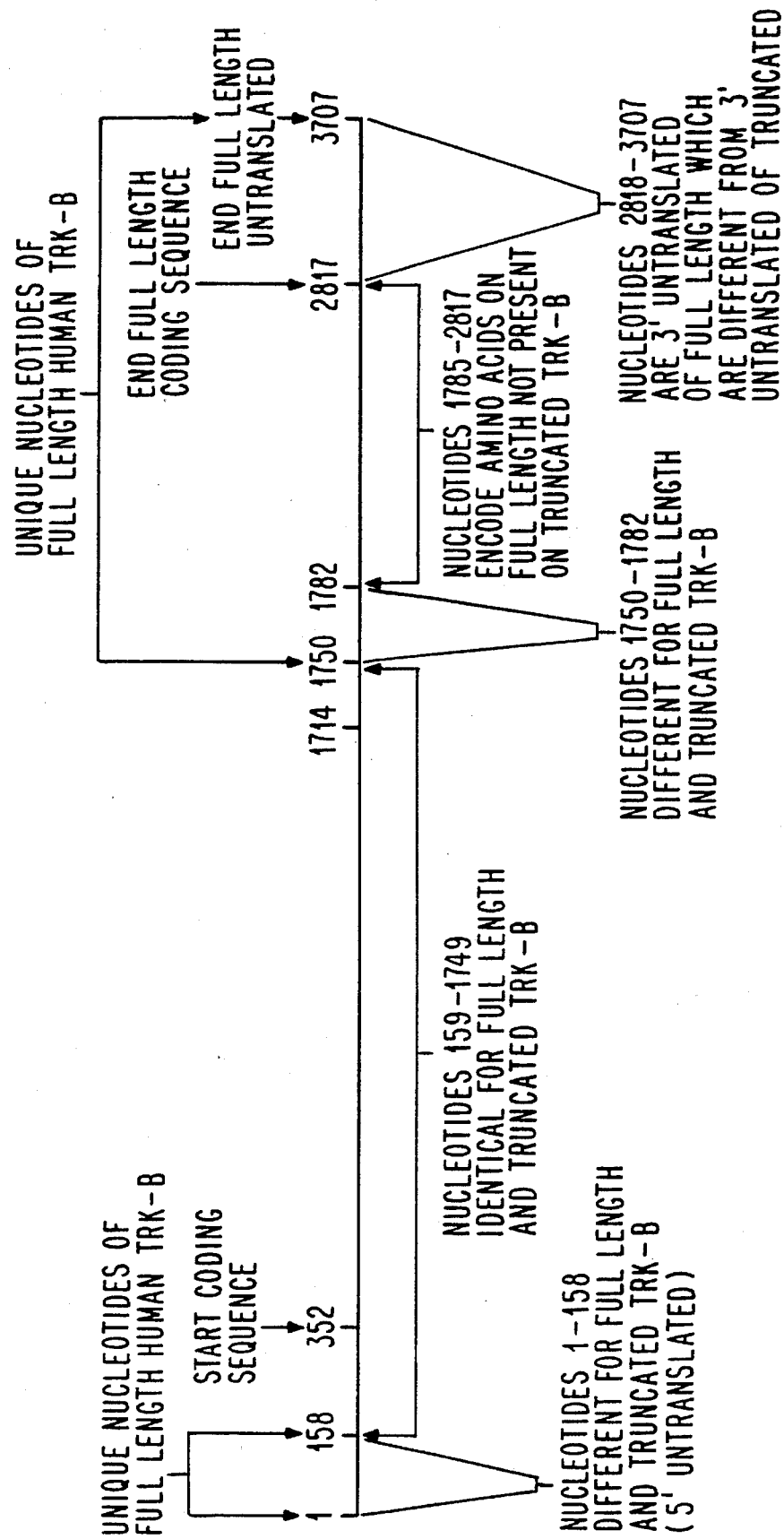
FIG. 1 is a map of the cDNA sequence encoding full length human TRK-B and a comparison of it to truncated human TRK-B showing areas of common sequences and areas where the sequences differ including sequences of full length TRK-B where no corresponding sequences from truncated TRK-B exist.

As used herein, the term "intracellular domain of full length human TRK-B" is meant to refer to the portion of the carboxy terminus of the full length human TRK-B protein which is different from that of the truncated form of the protein. Specifically, intracellular domain of full length human TRK-B is meant to refer to the portion of the full length human TRK-B protein which occurs after amino acid encoded by nucleotide 1749 of SEQ ID NO: 1 (amino acid 466). Thus the intracellular domain of full length human TRK-B is encoded by the nucleotide sequence which occurs 3' to nucleotide 1749 of SEQ ID NO: 1. While the truncated form of the protein has a small peptide sequence on the carboxy end of the molecule extending 23 amino acids beyond the transmembrane region, the full length human TRK-B to has an amino acid sequence that extends 367 amino acids beyond the transmembrane domain which includes the carboxy 356 amino acids not present in the truncated form. The term "intracellular domain of full length human TRK-B" is meant to refer to the portion of intracellular domain of full length human TRK-B which is unique relative to the truncated form of the protein. The intracellular domain of full length human TRK-B as defined herein consists of amino acids encoded by nucleotides 1750–2818 of SEQ ID NO: 1 (amino acids 466 to 822).

As used herein, the term "nucleotide sequence that encodes the intracellular domain of full length human TRK-B" is meant to refer to the nucleotide sequence that encodes the portion of the carboxy terminus of the full length human TRK-B protein which is different from that of the truncated form of the protein. Specifically, the nucleotide sequence that encodes the intracellular domain of full length human TRK-B is meant to refer to the portion of the coding sequence that encodes full length human TRK-B protein which occurs after amino acid nucleotide 1749 of SEQ ID NO: 1. The term "nucleotide sequence that encodes the intracellular domain of full length human TRK-B" is meant to refer to the portion of nucleotide sequence that encodes the intracellular domain of full length human TRK-B which is unique relative to the nucleotide sequence that encodes the truncated form of the protein. The nucleotide sequence that encodes the intracellular domain of full length human TRK-B as defined herein consists of nucleotides 1749 to 2828 of SEQ ID NO: 1.

As used herein, the term "3' UTR of full length human TRK-B message" is meant to refer to the 3' untranslated region of the messenger RNA, or cDNA produced therefrom, which encodes the full length human TRK-B protein. The 3' untranslated region of full length human TRK-B message is different from that of the truncated form of the protein. The 3' UTR of full length TRK-B message consists of nucleotides 2829 to 3207 of SEQ ID NO: 1.

As used herein, the term "5' UTR of full length human TRK-B message" is meant to refer to the portion of the 5' untranslated region of the messenger RNA, or cDNA produced therefrom, which encodes the full length human TRK-B protein that is 5' to nucleotide 159 of SEQ ID NO: 1. It has been discovered that the first 158 nucleotides of the 5' untranslated region of the messenger RNA which encodes the full length human TRK-B protein is different from that of the truncated form while the remaining 193 are the same. The term "5' UTR of full length human TRK-B" is meant to refer to the portion of 5' untranslated region from message that encodes full length human TRK-B which is unique relative to the 5' untranslated region from message that encodes the truncated form of the protein. The 5' UTR of full length TRK-B message consists of nucleotides 1 to 158 of SEQ ID NO: 1.

As used herein, the term "unique nucleotide sequences of full length TRK-B" is meant to refer to collectively as: nucleotide sequence that encodes the intracellular domain of full length human TRK-B, 3' UTR of full length human TRK-B message and 5' UTR of full length human TRK-B message as defined herein. Unique nucleotide sequences of full length TRK-B consists of nucleotides 1–158 and 1749–3207 of SEQ ID NO: 1.

Figure 2:
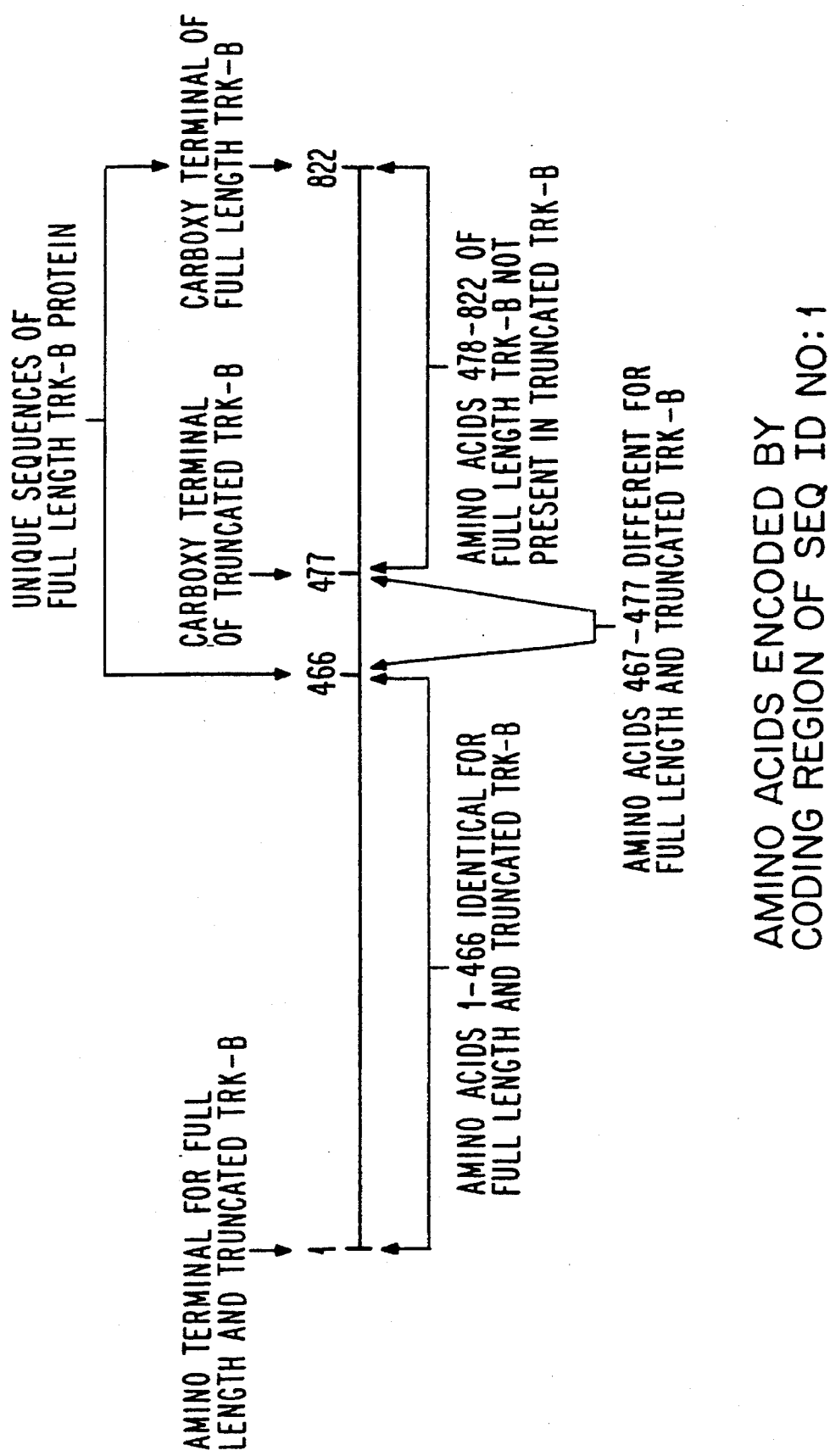
FIG. 2 is a map of the amino acid sequence of full length human TRK-B and a comparison of it to truncated human TRK-B showing areas of common sequences and areas where the sequences differ including sequences of full length TRK-B where no corresponding sequences from truncated human TRK-B exist.

The following information refers to particular nucleotides of SEQ ID NO: 1 and as set out in FIG. 1 and FIG. 2.

Nucleotides 1–158 of SEQ ID NO: 1 are 5' untranslated which are unique to full length human TRK-B relative to truncated form.

Nucleotides 159–1749 of SEQ ID NO: 1 are shared by both the full length human TRK-B and truncated forms.

Nucleotides 1750–1782 of SEQ ID NO: 1 encode amino acids of the full length human TRK-B which are different from those of the truncated form.

Nucleotides 1783–2817 of SEQ ID NO: 1 encode amino acids of full length human TRK-B that have no corresponding amino acids on the truncated form.

Nucleotides 2818–3707 of SEQ ID NO: 1 are 3' untranslated which are unique to full length human TRK-B relative to truncated form.

The coding sequences for both full length human TRK-B and truncated forms start at 352 of the hard copy.

The coding sequences for full length human TRK-B ends at 2817 of the hard copy.

Amino acids 1–466 encoded by nucleotides 352–1749 of SEQ ID NO: 1 are shared by both full length human TRK-B and truncated forms.

Amino acids 467–477 of full length human TRK-B and encoded by nucleotides 1750–1782 of SEQ ID NO: 1 are different from the truncated form.

Amino acids 478–822 of full length human TRK-B encoded by nucleotides 21783–2817 of SEQ ID NO: 1 have no corresponding amino acids on the truncated form.

The carboxy terminal amino acid for the full length human TRK-B is amino acid 822.

The present invention relates to the discovery of the nucleotide sequence of mRNA that encodes the full length isoform of the human neurotrophic receptor TRK-B and particularly the discovery of unique nucleotide sequences relative to those which encode the truncated form of human TRK-B. The full length isoform of the human neurotrophic receptor TRK-B has been observed to have tyrosine kinase activity and it is the intracellular portion of the molecule where such activity resides. It has been discovered that the presence of full length TRK-B in neuroblastoma is correlative with aggressive forms of neuroblastoma. The discovery of the sequence encoding the full length TRK-B allows for controlled studies of the BDNF-binding properties and tyrosine kinase activity of TRK-B in cells and as an isolated protein. The discovery of the entire coding sequence of the full length TRK-B allows for the production of full length TRK-B in cells. The cells can either be used in assays and methods to evaluate compounds for the ability to bind to and or modulate the activity of full length human TRK-B. The discovery of the sequence encoding the full length human TRK-B allows for the identification of neuroblastomas which express the full length version as distinguished from the truncated form, which is known. Cells transformed with DNA encoding full length TRK-B can be used as a source for the purification of isolated, full length TRK-B protein. Any of the methods and assays described herein may be performed using kits. Kits according to the invention comprise containers which contain reagents necessary to perform such assays.

The nucleotide sequence of a cDNA that encodes the full length TRK-B protein has been determined including the nucleotide sequence that encodes the 5' and 3' untranslated sequences and the full length protein which includes a carboxy terminal portion that makes up the intracellular domain which is responsible for the tyrosine kinase activity of the molecule. A comparison of the nucleotide sequence of cDNA that encodes full length TRK-B reveals unique nucleotide sequences relative to the nucleotide sequence of cDNA that encodes the truncated human TRK-B. These unique sequences are found at the 5' untranslated region, at the carboxy terminal of the protein and at the 3' untranslated region. As noted above, unique nucleotide sequences of full length TRK-B consists of nucleotides 1–158 and 1749–3207 of SEQ ID NO: 1.

Nucleic acid molecules which encode the full length TRK-B protein may be used to transfect cells that do not produce the full length TRK-B protein endogenously. Such transformed cells can be used in binding studies to identify other ligands in addition to BDNF including receptor antagonists. Known modulators of ligand/TRK-B binding activity such as K252b (Calbiochem Corp., LaJolla, Calif.) may be analyzed in transformed cells and used as control inhibitors in screens to identify test compounds with modulate binding activity. Further, the transformed cells can be used to study the tyrosine kinase activity of TRK-B and to identify compounds that modulate the tyrosine kinase activity such as inhibitors and stimulators. Known modulators of tyrosine kinase activity such as K252a (Calbiochem Corp. LaJolla, Calif.) may be analyzed in transformed cells and used as control inhibitors in screens to identify test compounds with inhibitory activity.

Examples of cells useful for transfecting with DNA that encodes full length human TRK-B in order to express full length TRK-B include NGP, NMB, NLF and SK-N-SH, each of which is readily available.

Examples of genetic constructs useful for transfecting with cells with DNA that encodes full length human TRK-B in order to express full length TRK-B include SEQ ID NO: 1 operable linked to a promoter that is functional in the cell line into which the constructs are transfected. Examples of constitutive promoters include promoters from cytomegalovirus or SV40. Examples of inducible promoters include mouse mammary leukemia virus or metallothionein promoters. Those having ordinary skill in the art can readily produce genetic constructs useful for transfecting with cells with DNA that encodes full length human TRK-B from readily available starting materials.

Binding studies may be done using known compounds that bind to TRK-B such as BDNF and comparing the binding affinity of test compounds to the receptor when competing with BDNF. Compounds which bind to the receptor can then be tested to determine if they induce kinase activity or if they are receptor antagonists which bind to the receptor but do not induce kinase activity.

Binding studies using transformed cells are well known and can be performed for example using labelled ligand in competitive binding assays with unlabelled ligands or using antibodies against unbound receptor to detect whether a compound is bound. K252b has been observed to inhibit binding of BDNF to TRK-B.

Kinase activity can be detected as follows. After contacting cells that include TRK-B with a ligand such as BDNF in the presence or absence of a test compound or inhibitor such as K252a, the TRK-B is immunoprecipitated with an anti-TRK-B antibody. A Western blot is performed with the immunoprecipitated material and an anti-phosphotyrosine antibody is used to probe the Western. If the immunoprecipitated TRK-B is reactive with the anti-phosphotyrosine antibody, it indicates that the kinase activity induced by ligand binding resulted in autophosphorylation.

Nucleic acid molecules which encode the full length human TRK-B protein may be used to transfect or transform cells that do not produce the full length human TRK-B protein endogenously in order to generate recombinant cells which produce recombinant full length human TRK-B having SEQ ID NO: 2 which may then be isolated. Isolated full length human TRK-B may be used in binding studies to identify other ligands in addition to BDNF that bind to the receptor. In addition, isolated full length human TRK-B may be used to generate monoclonal antibodies that specifically bind to an epitope of the intracellular domain. Binding studies using isolated protein are well known and can be performed for example using labelled ligand in competitive binding assays with unlabelled ligands or using antibodies against unbound receptor to detect whether a compound is bound.

Using the information disclosed herein, the nucleic acid sequence encoding full length human TRK-B protein may be isolated by routine means using readily available starting materials. A nucleic acid molecule with the nucleotide sequence of SEQ ID NO: 1 can be synthesized by routine means. Alternatively, a cDNA expression library may be generated from mRNA obtained from cells known to express the full length human TRK-B. Antibodies that specifically bind to epitopes on the intracellular domain of full length human TRK-B protein may then be used to identify clones which express the full length human TRK-B protein. Alternatively, the nucleotide sequence shown in SEQ ID NO: 1 may be used to generate probes useful to screen a cDNA library generated from mRNA obtained from cells known to express the full length human TRK-B protein. Using the information in SEQ ID NO: 1, DNA molecules that encode full length human TRK-B protein may be isolated by those having ordinary skill in the art from readily available starting material routine techniques. Isolation of a DNA sequence encoding full length human TRK-B protein permits the production of full length human TRK-B protein using recombinant techniques now known in the art.

Nucleic acid molecules that comprise nucleotide sequences that encode full length human TRK-B protein can be obtained from human genetic material or can be prepared chemically using nucleotide sequence synthesizer or other standard techniques. When the coding DNA is prepared synthetically, advantage can be taken of known codon preferences of the intended host where the DNA is to be expressed.

One having ordinary skill in the art can, using well known techniques and the information disclosed herein, obtain a DNA molecule encoding the full length human TRK-B protein and insert that DNA molecule into a commercially available expression vector for use in well known expression systems. For example, the commercially available plasmid pSE420 (Invitrogen, San Diego, Calif.) may be used for production in *E. coli*. The commercially available plasmid pYES2 (Invitrogen, San Diego, Calif.) may be used for production in *S. cerevisiae* strains of yeast. The commercially available MaxBac™ (Invitrogen, San Diego, Calif.) complete baculovirus expression system may be used for production in insect cells. The commercially available plasmid pcDNA I (Invitrogen, San Diego, Calif.) may be used for production in mammalian cells such as Chinese Hamster Ovary cells.

One having ordinary skill in the art can use these commercial expression vectors systems or others to produce full length human TRK-B protein using routine techniques and readily available starting materials.

One having ordinary skill in the art may use other commercially available expression vectors and systems or produce vectors using well known methods and readily available starting materials. Expression systems containing the requisite control sequences, such as promoters and polyadenylation signals, and preferably enhancers, are readily available and known in the art for a variety of hosts. See e.g., Sambrook et al., *Molecular Cloning a Laboratory Manual*, Second Ed. Cold Spring Harbor Press (1989). Thus, the desired proteins can be prepared in both prokaryotic and eukaryotic systems, resulting in a spectrum of processed forms of the protein.

The most commonly used prokaryotic system remains *E. coli*, although other systems such as *B. subtilis* and Pseudomonas are also useful. Suitable control sequences for prokaryotic systems include both constitutive and inducible promoters including the lac promoter, the trp promoter, hybrid promoters such as tac promoter, the lambda phage Pl promoter. In general, foreign proteins may be produced in these hosts either as fusion or mature proteins. When the desired sequences are produced as mature proteins, the sequence produced may be preceded by a methionine which is not necessarily efficiently removed. Accordingly, the peptides and proteins claimed herein may be preceded by an N-terminal Met when produced in bacteria. Moreover, constructs may be made wherein the coding sequence for the peptide is preceded by an operable signal peptide which results in the secretion of the protein. When produced in prokaryotic hosts in this matter, the signal sequence is removed upon secretion.

A wide variety of eukaryotic hosts are also now available for production of recombinant foreign proteins. As in bacteria, eukaryotic hosts may be transformed with expression systems which produce the desired protein directly, but more commonly signal sequences are provided to effect the secretion of the protein. Eukaryotic systems have the additional advantage that they are able to process introns which may occur in the genomic sequences encoding proteins of higher organisms. Eukaryotic systems also provide a variety of processing mechanisms which result in, for example, glycosylation, carboxy-terminal amidation, oxidation or derivatization of certain amino acid residues, conformational control, and so forth.

Commonly used eukaryotic systems include, but is not limited to, yeast, fungal cells, insect cells, mammalian cells, avian cells, and cells of higher plants. Suitable promoters are available which are compatible and operable for use in each of these host types as well as are termination sequences and enhancers, as e.g. the baculovirus polyhedron promoter. As above, promoters can be either constitutive or inducible. For example, in mammalian systems, the mouse metallothionein promoter can be induced by the addition of heavy metal ions.

The particulars for the construction of expression systems suitable for desired hosts are known to those in the art. For recombinant production of the protein, the DNA encoding it is suitably ligated into the expression vector of choice and then used to transform the compatible host which is then cultured and maintained under conditions wherein expression of the foreign gene takes place. The protein of the present invention thus produced is recovered from the culture, either by lysing the cells or from the culture medium as appropriate and known to those in the art.

One having ordinary skill in the art can, using well known techniques, isolate and purify the full length human TRK-B protein produced using such expression systems. Essentially pure and isolated protein having an amino acid sequence of SEQ ID NO: 2 can be obtained and used to generate antibodies which specifically bind to full length human TRK-B. The pure and isolated protein having the amino acid sequence disclosed in SEQ ID NO: 2 may be prepared as a crystal to allow for the three dimensional conformation of full length human TRK-B to be solved. It is contemplated that the intracellular domain of full length human TRK-B, that is the portion of the protein present in full length human TRK-B but absent in truncated TRK-B, results in changes in the conformation and configuration of the extracellular domain of the full length human TRK-B relative to the conformation and configuration of the extracellular domain of truncated human TRK-B. Such differences in the configuration of the extracellular domain may affect ligand binding activity and kinetics.

The cDNA that encodes the full length human TRK-B may be used as a molecular marker in electrophoresis assays in which cDNA from a sample is separated on an electrophoresis gel and full length human TRK-B specific probes are used to identify bands which hybridize to such probes. Specifically, SEQ ID NO: 1 may be used as a molecular marker in electrophoresis assays in which cDNA from a sample is separated on an electrophoresis gel and full length human TRK-B specific probes are used to identify bands which hybridize to them, indicating that the band has a nucleotide sequence complementary to the sequence of the probes. The isolated nucleic acid molecule provided as a size marker will show up as a positive band which is known to hybridize to the probes and thus can be used as a reference point to the size of cDNA that encodes full length human TRK-B. Electrophoresis gels useful in such an assay include standard polyacrylamide gels as described in Sambrook et al., *Molecular Cloning a Laboratory Manual*, Second Ed. Cold Spring Harbor Press (1989) which is incorporated herein by reference.

The nucleotide sequence in SEQ ID NO: 1 may be used to design probes, primers and antisense molecules which specifically hybridize to the unique nucleotide sequences of full length TRK-B. Probes, primers and antisense molecules which specifically hybridize to nucleotide sequence that encodes the intracellular domain of full length human TRK-B, 3' UTR of full length human TRK-B message and 5' UTR of full length human TRK-B message may be designed.

It has been discovered that the most aggressive neuroblastomas, those which are generally associated with "poor outcomes", express full length human TRK-B. The expression of full length human TRK-B correlates significantly with the presence of amplified N-myc, another indicator of aggressive neuroblastoma.

Identification of neuroblastomas which expression full length human TRK-B indicates that the neuroblastoma is likely to be aggressive and therefore the clinician should pursue an aggressive therapeutic approach. Such information allows for the characterization of the neuroblastoma which is then used to prescribe the course of therapy to be undertaken.

Aspects of the present invention include various methods of determining whether a neuroblastoma has full length human TRK-B by sequence-based molecular analysis. Several different methods are available for doing so including those using Polymerase Chain Reaction (PCR) technology, restriction fragment length analysis using Southern blot technology and oligonucleotide hybridization technology.

Furthermore, the invention relates to probes, oligonucleotide primers, and monoclonal antibodies used in the methods of identifying neuroblastoma which express full length human TRK-B. In addition, the invention relates to diagnostic kits which comprise such components.

Neuroblastoma that express full length human TRK-B can be distinguished from neuroblastoma that do not express full length human TRK-B by identifying the presence of unique nucleotide sequences of full length human TRK-B including nucleotide sequence that encodes the intracellular domain of full length human TRK-B, 3' UTR of full length human TRK-B message and 5' UTR of full length human TRK-B message. These DNA sequences are not present as mRNA in neuroblastoma that do not express TRK-B or that express truncated TRK-B only. Thus, sequence-based assays can be performed to identify whether or not mRNA sequences that encode the unique nucleotide sequences of full length human TRK-B are present in an sample obtained from neuroblastoma.

The sequence-based methods for determining the nature of neuroblastoma include, but are not limited to, polymerase chain reaction technology and oligonucleotide hybridization technology. Each of these methods are useful to distinguish neuroblastoma that express full length human TRK-B from neuroblastoma that do not express full length human TRK-B by detecting, in one way or another, the presence of unique nucleotide sequences of full length human TRK-B. The methods described herein are meant to exemplify how the present invention may be practiced and are not meant to limit the scope of invention. It is contemplated that other sequence-based methodology for detecting the presence of specific nucleotide sequences can be used to distinguish neuroblastoma that express full length human TRK-B from neuroblastoma that do not express full length human TRK-B as taught by the present invention.

A preferred method to identify neuroblastoma that express full length human TRK-B is to detect the presence of unique nucleotide sequences of full length human TRK-B in genetic material derived from cells identified as neuroblastoma using polymerase chain reaction (PCR) technology. PCR technology is practiced routinely by those having ordinary skill in the art and its uses in diagnostics are well known and accepted. Methods for practicing PCR technology are disclosed in "PCR Protocols: A Guide to Methods and Applications", Innis, M. A., et al. Eds. Academic Press, Inc. San Diego, Calif. (1990) which is incorporated herein by reference. Applications of PCR technology are disclosed in "Polymerase Chain Reaction" Erlich, H. A., et al., Eds. Cold Spring Harbor Press, Cold Spring Harbor, N.Y. (1989) which is incorporated herein by reference.

Those having ordinary skill in the art can readily prepare PCR primers in which at least one comprises a nucleotide sequence having at least 5 nucleotides which are identical or complementary to at least a fragment of unique nucleotide sequences of full length human TRK-B. That is, one having ordinary skill in that can readily design sets of primers which will only generate PCR products if a nucleic acid molecule is present which has the SEQ ID NO: 1 including unique nucleotidase of full length TRK-B.

Some simple rules aid in the design of efficient primers. Typical primers are 18–28 nucleotides in length having 50% to 60% g+c composition. The entire primer is preferably complementary to the sequence it must hybridize to. Preferably, primers generate PCR products 100 basepairs to 2000 base pairs. However, it is possible to generate products of 50 to up to 10 kb and more. At least one of the primers must hybridize to at least a 5 nucleotide fragment of a unique nucleotide sequence of full length TRK-B.

PCR technology allows for the rapid generation of multiple copies of nucleotide sequences by providing 5' and 3' primers that hybridize to sequences present in a nucleic acid molecule, and further providing free nucleotides and an enzyme which fills in the complementary bases to the nucleotide sequence between the primers with the free nucleotides to produce a complementary strand of DNA. The enzyme will fill in the complementary sequences adjacent to the primers. If both the 5' primer and 3' primer hybridize to nucleotide sequences on the complementary strands of the same fragment of nucleic acid, exponential amplification of a specific double-stranded product results. If only a single primer hybridizes to the nucleic acid molecule, linear amplification produces single-stranded products of variable length.

In the present invention, neuroblastoma that express full length TRK-B can be identified by detecting a PCR fragment that is generated by a set of primers which are each complementary to nucleotide sequences on opposing strands of a full length human TRK-B message and which include at least one primer that is identical or complementary to unique nucleotide sequences of full length human TRK-B. Using such a set of primers, only those nucleic acid molecules which comprise unique nucleotide sequences of full length human TRK-B can be used to generate a double stranded PCR product. This is accomplished performing PCR on a sample of genetic material derived from neuroblastoma cells using the above described set of PCR primers.

To perform this method, RNA is extracted from neuroblastoma cells and used to make cDNA using well known methods and readily available starting materials. The cDNA is combined with the primers, free nucleotides and enzyme following standard PCR protocols. The mixture undergoes a series of temperature changes. If cDNA with sequence that encodes the intracellular domain is present, that is, if both primers hybridize to sequences on the same molecule, the molecule comprising the primers and the intervening complementary sequences will be exponentially amplified. The amplified DNA can be easily detected by a variety of well known means. If cDNA with unique nucleotide sequences of full length human TRK-B is not present, no double stranded DNA molecule will be exponentially amplified. The PCR technology therefore provides an extremely easy, straightforward and reliable method of detecting the presence of unique nucleotide sequences of full length human TRK-B.

Accordingly, a preferred method of determining whether a cell is neuroblastoma that expresses full length TRK-B is by using PCR technology on cDNA to detect the presence of unique nucleotide sequences of full length human TRK-B. Sets of primers are prepared which consist of primers that hybridize to opposing strands of complementary nucleotide sequences. At least one of the primers hybridizes to unique nucleotide sequences of full length human TRK-B or the complement thereof. In preferred embodiments, sets of primers are prepared which consist of primers that hybridize to unique nucleotide sequences of full length human TRK-B 5' and 3' of the portion of the full length TRK-B sequence that encodes the intracellular domain. Primers may be designed based upon the sequence disclosed in SEQ ID 1.

If unique nucleotide sequences of full length human TRK-B are present between primers, multiple copies of the cDNA transcribed from it will be made. If the sequence is not present, PCR will not generate a discrete detectable double stranded product. Amplified DNA may be detected by several well known means. The preferred method for detecting the presence of amplified DNA is to separate the PCR reaction material by gel electrophoresis and stain the gel with ethidium bromide in order to visual the amplified DNA if present. A size standard of the expected size of the amplified DNA is preferably run on the gel as a control. The size of the expected size standard is the length of each of the primers plus the length of the sequence there between which is amplified by the primers.

In some instances, such as when unusually small amounts of RNA are recovered and only small amounts of cDNA are generated therefrom, it is desirable or necessary to perform a PCR reaction on the first PCR reaction product. That is, if difficult to detect quantities of amplified DNA are produced by the first reaction, a second PCR can be performed to make multiple copies of DNA sequences of the first amplified DNA. A nested set of primers are used in the second PCR reaction. The nested set of primers hybridize to sequences downstream of the 5' primer and upstream of the 3' primer used in the first reaction.

The present invention includes oligonucleotides which are useful as primers for performing PCR methods to amplify unique nucleotide sequences of full length human TRK-B. Accordingly, the present invention includes PCR primers that hybridize to a nucleotide sequence of at least 5 nucleotides in length from nucleotides 1–158 and 1749–3207 of SEQ ID NO: 1 or a complement thereof. Preferred primers hybridize to the 5' end or the 3' end of the portion of the full length TRK-B sequence that encodes the intracellular domain. Primers are designed based upon the sequence disclosed in SEQ ID 1. Preferably, the PCR primers of the present invention are provided as sets in a single composition comprising which include both 5' primer add 3' primer, each of which is identical to or hybridizes to a unique nucleotide sequences of full length human TRK-B.

According to the invention, screening kits can be assembled which are useful to practice methods of distinguishing neuroblastomas that express full length human TRK-B from those that do not express full length human TRK-B. Such kits comprise oligonucleotides which are useful as primers for performing PCR methods to amplify sequences that encode the intracellular domain. Accordingly, screening kits of the present invention comprise PCR primers that are identical to or hybridize to unique nucleotide sequences of full length human TRK-B. Screening kits of the present invention comprise PCR primers that are designed based upon the sequence disclosed in SEQ ID 1. The preferred screening kit of the present invention comprises PCR primers to the portion of the full length TRK-B sequence that encodes the intracellular domain. It is preferred that screening kits according to the present invention comprise a size marker to be run as a standard on a gel used to detect the presence of amplified DNA. The size marker is the same size as the DNA generated by the primers in the presence of the coding sequence for the intracellular domain.

Another method of detecting the transcription of specific DNA sequences associated with expression of a protein is by oligonucleotide hybridization technology. Oligonucleotide hybridization technology is well known to those having ordinary skill in the art. Briefly, detectable probes which contain a specific nucleotide sequence that will hybridize to unique nucleotide sequences of full length human TRK-B but which will not hybridize to genetic material that does not contain unique nucleotide sequences of full length human TRK-B. The cell's RNA or cDNA made from RNA is fixed, usually to filter paper or the like. The probes are added and maintained under conditions that permit hybridization only if the probes fully complement the fixed genetic material. The conditions are sufficiently stringent to wash off probes in which only a portion of the probe hybridizes to the fixed material. Detection of the probe on the washed filter indicate complementary sequences. One having ordinary skill in the art, using the sequence information disclosed herein and the disclosure of the breakpoint location including adjacent genes can devise a variety of protocols that use oligonucleotide hybridization technology to identify neuroblastoma with full length human TRK-B expression. Alternatively, it is contemplated that oligonucleotide hybridization can be performed in situ.

According to the preferred method of using oligonucleotide hybridization techniques to identify whether of not a neuroblastoma expresses full length human TRK-B, a probe is provided which hybridizes to the RNA encoding the intracellular domain or cDNA thereof. The probes may comprise nucleotide sequences of 10–200 base pairs or more which hybridize to unique nucleotide sequences of full length human TRK-B which are nucleotides 1–158 and 1749–3701 of SEQ ID NO: 1. The probes preferably comprise nucleotide sequences of 20–150 base pairs, more preferably 50–100. Thus, the probe hybridizes to nucleotide sequences that encode the intracellular domain. The probe is preferably labelled with a radioisotope. The oligonucleotide probe must contain at least a sequence that hybridizes to 5 nucleotide fragment of a unique nucleotide sequence of full length TRK-B. Those having ordinary skill in the art can readily prepare oligonucleotide probes having at least 5 nucleotides which are identical or complementary to at least a fragment of unique nucleotide sequences of full length human TRK-B. That is, one having ordinary skill in that can readily design oligonucleotide probes which will hybridize to a nucleic molecule which has the SEQ ID NO: 1 including unique nucleotidase of full length TRK-B but not to an nucleic acid molecule encoding the truncated form.

RNA is extracted from cells and used to make cDNA. The cDNA is blotted to nitrocellulose or nylon filters and after treatment with prehybridizing buffer, probe is added for hybridization. The cDNA blot is then washed under conditions that are sufficiently stringent to permit hybridization to take place only if the probe is fully complementary to the cDNA. The cDNA which includes unique nucleotide sequences of full length human TRK-B is present if the probe remains hybridized after washing, indicating neuroblastoma with full length TRK-B expression.

The present invention includes labelled oligonucleotides which are useful as probes for performing oligonucleotide hybridization methods to identify neuroblastoma that express full length TRK-B. Accordingly, the present invention includes labelled probes that hybridize to unique nucleotide sequences of full length human TRK-B. The labelled probes of the present invention are labelled with radiolabelled nucleotides or are otherwise detectable by readily available nonradioactive detection systems. In some preferred embodiments, probes comprise oligonucleotides consisting of between 10 and 100 nucleotides. In some preferred, probes comprise oligonucleotides consisting of between 10 and 50 nucleotides. In some preferred, probes comprise oligonucleotides consisting of between 12 and 20 nucleotides. The probes preferably contain nucleotide sequence completely identical or complementary to a fragment of a unique nucleotide sequences of full length human TRK-B.

According to the invention, screening kits can be assembled which are useful to practice oligonucleotide hybridization methods of distinguishing neuroblastoma that express full length human TRK-B from neuroblastoma that do not express full length human TRK-B. Such screening kits comprise a labelled oligonucleotide which hybridizes to unique nucleotide sequences of full length human TRK-B. Accordingly, screening kits of the present invention comprise a labelled probe as described above. It is preferred that labelled probes of the oligonucleotide diagnostic kits according to the present invention are labelled with a radionucleotide. The oligonucleotide hybridization-based screening kits according to the invention preferably comprise DNA samples that represent positive and negative controls. A positive control DNA sample is one that comprises a nucleic acid molecule which has a nucleotide sequence that is fully complementary to the probes of the kit such that the probes will hybridize to the molecule under assay conditions. A negative control DNA sample is one that comprises at least one nucleic acid molecule, the nucleotide sequence of which is partially complementary to the sequences of the probe of the kit. Under assay conditions, the probe will not hybridize to the negative control DNA sample.

In addition to sequence-based methods of identifying neuroblastoma that express full length TRK-B, the present invention relates to monoclonal antibody-based screening techniques. Monoclonal antibodies of the present invention are directed at epitopes of the intracellular domain of full length human TRK-B which consists of amino acids 466 to 822 of SEQ ID NO: 1. Monoclonal antibodies that bind to the full length but that do not cross-react with the truncated protein can be used to detect the presence of the full length protein. Monoclonal antibody-based kits which contain monoclonal antibodies that specifically bind to the intracellular domain of the full length human TRK-B and control samples are within the scope of the present invention. One having ordinary skill in the art using standard techniques can generate such monoclonal antibodies and use them in an assay to determine whether the neuroblastoma has full length human TRK-B. Antibodies which bind to the intracellular domain of full length human TRK-B may be used in purification procedures to isolate full length human TRK-B from sources which produce the protein endogenously, recombinantly or both endogenously and recombinantly.

Another aspect of the present invention is a method of treating an individual suspected of suffering from neuroblastoma which comprises the step of administering to such an individual a therapeutically effective amount of antibody which binds to the intracellular domain of full length human TRK-B. As used herein, the term "effective amount of antibodies" is meant to refer to the amount of antibody necessary to eliminate or inhibit growth and proliferation of neuroblastoma that express full length human TRK-B in the individual. Effective amounts include both the amount effective to eliminate the neuroblastoma as well as the amount effective to slow the growth and proliferation relative to the rate of progress that would be observed in the absence of the antibodies.

Those having ordinary skill in the art can produce monoclonal antibodies which specifically bind to the intracellular domain of the full length human TRK-B protein and are useful as therapeutics using standard techniques and readily available starting materials. The techniques for producing monoclonal antibodies are outlined in Harlow, E. and D. Lane, (1988) *ANTIBODIES: A Laboratory Manual*, Cold Spring Harbor Laboratory, Cold Spring Harbor N.Y., which is incorporated herein by reference, provide detailed guidance for the production of hybridomas and monoclonal antibodies which specifically bind to target proteins. Briefly for example, full length human TRK-B protein, or an immunogenic fragment thereof including the carboxy terminal portion, is injected into mice. The spleen of the mouse is removed, the spleen cells are isolated and fused with immortalized mouse cells. The hybrid cells, or hybridomas, are cultured and those cells which secrete antibodies are selected. The antibodies are analyzed and, if found to specifically bind to the intracellular domain of the full length human TRK-B, the hybridoma which produces them is cultured to produce a continuous supply of antibodies.

Another aspect of the present invention provides an isolated nucleic acid molecule that comprises a nucleotide sequence that is identical complementary to unique nucleotide sequences of full length human TRK-B and pharmaceutical compositions which contain such nucleic acid molecules. Nucleic acid molecules that comprises a nucleotide sequence that is identical or complementary to a unique nucleotide sequences of full length human TRK-B may be used in methods for modulating the activity of RNA that encodes full length human TRK-B. Accordingly, nucleic acid molecules that comprises a nucleotide sequence that is identical or complementary to unique nucleotide sequences of full length human TRK-B relate to the field of "antisense" compounds, compounds which are capable of specific hybridization with a nucleotide sequence of an RNA molecule.

As used herein, the term "anti-full length human TRK-B antisense compound" is meant to refer to nucleic acid molecules that comprises a nucleotide sequence that is identical or complementary to unique nucleotide sequences of full length human TRK-B. Preferred anti-full length human TRK-B antisense compound include those which comprise nucleotide sequences that are identical to a nucleotide sequence that encodes a portion of the intracellular domain of full length human TRK-B. Anti-full length human TRK-B antisense compounds are capable of specific hybridization with a nucleotide sequence of an RNA molecule and thereby block translation of mRNA that encodes full length human TRK-B, thus inhibiting production of the protein.

The anti-full length human TRK-B antisense compounds of the present invention are useful to inhibit expression of human full length human TRK-B in neuroblastoma. It is the general object of such therapeutic approaches to interfere with or otherwise modulate gene expression leading to full length human TRK-B production.

One method for inhibiting specific gene expression which has been adopted to some degree is the "antisense" approach, where oligonucleotide analogues complementary to a specific, target, messenger RNA, mRNA sequence are used. A number of workers have reported such attempts. Pertinent reviews include C. A. Stein & J. S. Cohen, *Cancer Research*, vol. 48, pp. 2659–2668 (1988); J. Walder, *Genes & Development*, vol. 2, pp. 502–504 (1988); C. J. Marcus-Sekura, *Anal. Biochemistry*, vol. 172,289–295 (1988); G. Zon, *Journal of Protein Chemistry*, vol. 6, pp-131–145 (1987); G. Zon, *Pharmaceutical Research*, vol. 5, pp. 539–549 (1988); A. R. Van der Krol, J. N. Mol, & A. R. Stuitje, *BioTechniques*, vol. 6, pp. 958–973 (1988) and D. S. Loose-Mitchell, *TIPS*, vol. 9, pp. 45–47 (1988). Each of the foregoing provide background concerning general antisense theory and prior techniques.

Antisense compositions according to the present invention comprise oligonucleotide molecules which are complementary to the nucleotide sequence of the DNA molecule that encodes full length human TRK-B. In preferred embodiments, antisense compositions according to the present invention comprise oligonucleotide molecules which are complementary to the nucleotide sequence of the DNA molecule that encodes the intracellular domain of full length human TRK-B. In preferred embodiments, antisense compositions according to the present invention comprise oligonucleotide molecules which are complementary to a portion of SEQ ID NO: 1 from X to Y at least 5, preferably 5–200, more preferably 5–50, most preferably 8 to 25, preferably 12 nucleotides in length. The oligonucleotides in accordance with this aspect of the invention preferably comprise from about 5 to about 200 nucleotides. The oligonucleotides in accordance with this aspect of the invention more preferably comprise from about 5 to about 50 nucleotides. It is more preferred that such oligonucleotides comprise from about 8 to 25 nucleotides, and still more preferred to have from about 12 to 25 nucleotides.

The oligonucleotides used in accordance with this aspect of the invention may be conveniently and routinely made through the well-known technique of solid phase synthesis using the information provided in SEQ ID NO: 1. Equipment for such synthesis is sold by several vendors including Applied Biosystems. Any other means for such synthesis may also be employed, however the actual synthesis of the oligonucleotides are well within the talents of the one having ordinary skill in the art. It is also well known to use similar techniques to prepare other oligonucleotides such as the phosphorothioates and alkylated derivatives.

In accordance with this aspect of the present invention, persons of ordinary skill in the art will understand that messenger RNA includes not only the information to encode a protein using the three letter genetic code, but also associated ribonucleotides which form a region known to such persons as the 5'-untranslated region, the 3'-untranslated region, the 5' cap region and intron/exon junction ribonucleotides. Thus, oligonucleotides may be formulated in accordance with this invention which are targeted wholly or in part to these associated ribonucleotides as well as to the informational ribonucleotides. In preferred embodiments, the oligonucleotide is specifically hybridizable with a transcription initiation site, a translation initiation site, an intron/ exon junction or sequences in the 5'- or 3'-untranslated region or 5' cap region.

Oligonucleotides useful in the invention are complementary to the DNA or to the corresponding messenger RNA (mRNA) or pre-messenger RNA. Thus, the oligonucleotides in accordance with the invention preferably have one of the foregoing sequences or an effective portion thereof. Thus, it is preferred to employ any of these oligonucleotides as set forth above or any of the similar nucleotides which persons of ordinary skill in the art can prepare from knowledge of the preferred antisense targets for the modulation of full length human TRK-B production.

Pharmaceutical compositions according to the invention comprise a pharmaceutically acceptable carrier in combination with an active ingredient selected from the group consisting of antibodies and antisense molecules. The pharmaceutical compositions of the invention may be formulated by one having ordinary skill in the art with compositions selected depending upon the chosen mode of administration. Suitable pharmaceutical carriers are described in the most recent edition of *Remington's Pharmaceutical Sciences*, A. Osol, a standard reference text in this field.

The active ingredient is formulated based upon the nature of the ingredient and how it is to be administered. For parenteral administration, the active ingredient can be, for example, formulated as a solution, suspension, emulsion or lyophilized powder in association with a pharmaceutically acceptable parenteral vehicle. Examples of such vehicles are water, saline, Ringer's solution, dextrose solution, and 5% human serum albumin. Liposomes and nonaqueous vehicles such as fixed oils may also be used. The vehicle or lyophilized powder may contain additives that maintain isotonicity (e.g., sodium chloride, mannitol) and chemical stability (e.g., buffers and preservatives). The formulation is sterilized by commonly used techniques. For example, a parenteral composition suitable for administration by injection is prepared by dissolving 1.5% by weight of active ingredient in 0.9% sodium chloride solution.

The pharmaceutical compositions according to the present invention may be administered as a single doses or in multiple doses. The pharmaceutical compositions of the present invention may be administered either as individual therapeutic agents or in combination with other therapeutic agents. The treatments of the present invention may be combined with conventional therapies, which may be administered sequentially or simultaneously.

The pharmaceutical compositions may be administered by any means that enables the active agent to reach the agent's site of action in the body. Because proteins are subject to being digested when administered orally, parenteral administration, i.e., intravenous, subcutaneous, intramuscular, would ordinarily be used to optimize absorption. Intravenous is the preferred route of administration.

The dosage administered varies depending upon factors such as: pharmacodynamic characteristics; its mode and route of administration; age, health, and weight of the recipient; nature and extent of symptoms; kind of concurrent treatment; and frequency of treatment. Usually, a daily dosage of antibody can be about 5 µg to 5000 mg of antibody. In some preferred embodiments, 50 µg to 500 mg of antibody may be administered. In other preferred embodiments, 500 µg to 50 mg of antibody may be administered. In a preferred embodiment, 5 mg of antibody is administered. The pharmaceutical compositions may be administered in divided doses 1 to 6 times a day or in sustained release form is effective to obtain desired results.

In addition to neuroblastoma, full length human TRK-B has been reported to be present in other tumor types associated with the central and peripheral nervous systems. Megaloblastoma, which are brain tumors found in the cerebellum, and primitive neuroectodermal tumors, which are brain tumors found in the cerebrum, are each examples of tumor types associated with the central and peripheral nervous systems. Similarly, peripheral neuroepithithelioma is another tumor type associated with the central and peripheral nervous systems.

It is contemplated that the methods of the present invention and the compositions and kits useful for practicing such methods may be used in the detection and treatment of tumor types associated with the central and peripheral nervous systems which express full length human TRK-B. The primers, probes, full length clones and antibodies of the present invention may used in methods to distinguish tumor types associated with the central and peripheral nervous systems that express full length human TRK-B from those that do not. Likewise, the antisense compounds and antibodies may be used to treat individuals suffering from tumor types associated with the central and peripheral nervous systems that express full length human TRK-B.

Deficiencies in full length human TRK-B as a result of mutations for example ar linked to developmental abnormalities. Snider, W. D., (1994) CELL 77:627–638, discloses the results of knock out experiments which demonstrate that mutations which result in non-functioning or dysfunctional protein lead to moderate to severe developmental abnormalities which may correspond to neurologic diseases and syndromes. The present invention provides diagnostic means to determine whether an individual is a carrier or suffers from a mutation in the full length human TRK-B gene which may be responsible for genetic diseases which manifest themselves as neurologic disorders or conditions. According to the present invention, screening tests useful to distinguish cells which express full length human TRK-B from those that do not can be applied as diagnostic and screening tools to identify individuals who have express mutated full length human TRK-B. For example, the probes, primers, full length clones and antibodies discussed above and the methods to distinguish tumor types that express full length TRK-B from those that do not which employ each such reagents may be adapted to identify carriers of genetic diseases associated with expression of mutated full length human TRK-B as well as to diagnose individuals suffering from or susceptible to genetic diseases, such as for example Friedreich's ataxia, resulting from or correlative with expression of mutated full length human TRK-B. It is contemplated that the nucleic acid molecules disclosed herein as SEQ ID NO: 1 which encodes full length human TRK-B may be used in gene therapy protocols to treat individuals suffering from or susceptible to genetic diseases resulting from expression of mutated full length human TRK-B.

In another aspect of the invention, transgenic nonhuman animals, particularly transgenic mice, are generated. The transgenic animals according to the invention contain SEQ ID NO: 1. Such transgenic mice may be used as animal models for studying human TRK-B and for use in drug discovery efforts to find compounds that modulate human TRK-B/BDNF binding and human TRK-B tyrosine kinase activity. One having ordinary skill in the art using standard techniques, such as those taught in U.S. Pat No. 4,873,191 issued Oct. 10, 1989 Wagner and U.S. Pat. No. 4,736,866 issued Apr. 12, 1988 to Leder, both of which are incorporated herein by reference, can produce transgenic animals which produce the full length TRK-B protein and use the animals in drug discovery projects. Preferred animals are rodents, particularly rats and mice.

EXAMPLE

Full length TRK-B encodes a tyrosine kinase that binds to brain-derived neurotrophic factor (BDNF), as well as neurotrophin-3 (NT-3) and NT-4/5. The N-myc-amplified human neuroblastoma cell line, SMS-KCN, expresses both TRK-B and BDNF. Exogenous BDNF induces tyrosine phosphorylation of TRK-B as well as phosphorylation of phospholipase C-γ1, the extracellular signal-regulated kinases 1 and 2, and phosphatidylinositol-3 kinase. BDNF also induces expression of the immediate-early genes c-FOS and NGFI-A but not NGFI-B or NGFI-C. In addition, BDNF appears to promote cell survival and neurite outgrowth. SMS-KCN cells also express TRK-A, which is phosphorylated in response to nerve growth factor. However, the downstream TRK-A signaling is apparently defective.

In a series of 74 primary neuroblastomas, 36% express TRK-B mRNA, 68% express BDNF mRNA, and 31% express both. Truncated TRK-B appeared to be preferentially expressed in more-differentiated tumors (ganglioneuromas and ganglioneuroblastomas), whereas full-length TRK-B was expressed almost exclusively was immature neuroblastomas with N-myc amplification. These findings indicate that in TRK-B-expressing human neuroblastomas, BDNF promotes survival and induces neurite outgrowth in an autocrine or paracrine manner. The BDNF/TRK-B pathway may be particularly important for growth and differentiation of neuroblastomas with N-myc amplification.

It has been observed that a human neuroblastoma cell line, SMS-KCN, expresses both TRK-B and BDNF transcripts as well as TRK-A mRNA. BDNF induces immediate-early genes and phosphorylation of phospholipase C-γ1 (PLC-γ1), the extracellular signal-regulated kinases 1 and 2 (ERK1 and ERK2), and phosphatidylinositol-3 kinase (PI-3K) and appears to stimulate cell survival and neurite extension in an autocrine or paracrine manner. In contrast, NGF induces autophosphorylation of TRK-A, but the signaling pathway is deficient. Finally, truncated TRK-B appears to be preferentially expressed in more-differentiated tumors (ganglioneuromas and ganglioneuroblastomas), whereas full-length TRK-B is expressed in immature neuroblastomas with N-myc amplification.

Expression pattern of TRK-B and BDNF mRNAs in primary neuroblastomas. In contrast to results with neuroblastoma cell lines, expression of TRK-B was observed in 27 of 74 (36%) primary neuroblastomas (including five ganglioneuromas), but the expression pattern was complex. By extrapolation from studies of the mouse and rat TRK-B mRNA species, the −9.5 and −4.5-kb transcripts presumably encode the full-length product of human TRK-B, and other size transcripts encode the truncated form of the receptor without the tyrosine kinase domain. In each primary neuroblastoma expressing TRK-B, the intensities of both the −9.5 and −4.5-kb transcripts appeared to be equivalent. A clear −9.5-kb transcript was found in 7 of 10 (70%) neuroblastomas with N-myc amplification and in only 2 of 64 (3%) tumors without amplification ($x^2$=30.22; P<0.001). On the other hand, preferential expression of the putative truncated forms, especially of the −8.0-kb transcript, was observed in 18 of 64 (28%) neuroblastomas without N-myc amplification. Interestingly, five of five (100%) ganglioneuromas showed preferential expression of the putative truncated form of TRK-B mRNA.

BDNF mRNA expression was detected in 50 of 74 (68%) primary neuroblastomas. The frequencies were somewhat higher in advanced-stage (III or IV) neuroblastomas (22 of 28; 79%) and in mature ganglioneuromas (5 of 5; 100%) than in favorable-stage (I, II, or IV-S) neuroblastomas (23 of 41; 56%). Overall, 31% of the tumors had concordant expression of both TRK-B and BDNF. Seven of ten tumors with N-myc amplification had expression of both putative full-length TRK-B and BDNF, similar to the expression in the SMS-KCN cell line. Of the remaining 64 tumors, 16 (25%) had coexpression of BDNF and TRK-B, and all but 2 of these expressed predominantly truncated forms.

The BDNF/TRK-B signaling pathway in the SMS-KCN neuroblastoma cell line is functional. In contrast to the NGF/TRK-A pathway, the BDNF/TRK-B signaling pathway in neuronal cells has been unclear because a suitable cell line has not been available. It has been discovered an N-myc-amplified neuroblastoma cell line, SMS-KCN, expresses readily detectable endogenous levels of both TRK-B and BDNF mRNAs. This cell line also expresses TRK-A but not TRK-C, LNGFR, or NGF.

In SMS-KCN cells, exogenous BDNF induced phosphorylation of $p145^{TRK-B}$ and the downstream signaling pathway, including phosphorylation of PI-3K after 1 minute of incubation, phosphorylation of PKC-γ1, ERK1, and ERK2 after 5 minutes of incubation, and induction of the immediate-early genes of c-FOS and NGFI-A. The signaling cascade is very similar to that of the NGF/TRK-A) system in PC12 rat pheochromocytoma cells, except for the absence of induction of NGF1-B and NGF1-C. Since NGFI-B is expressed in many primary neuroblastoma tissues, the failure of this gene to be induced is probably not due to cell type or species differences.

BDNF seemed to promote cell survival and to induce neurite outgrowth of SMS-KCN cells. However, there are striking differences between the BDNF/TRK-B system in SMS-KCN cells and the NGF/TRK-A system in PC12 cells. BDNF may act on the SMS-KCN cells in an autocrine or paracrine manner, though it may not be saturated, while PC12 cells require exogenous NGF in order to differentiate. In addition, BDNF seems to induce neurite outgrowth and survival in SMS-KCN cells without substantial effects on cell growth, while NGF causes a decrease in the growth rate of PC12 cells.

Most primary neuroblastomas expressing both BDNF and TRK-B have N-myc amplification and overexpression, and this is true for the SMS-KCN cell line as well. Thus, the potential autocrine stimulation of these cells through the TRK-B/BDNF pathway may be a consequence of N-myc overexpression.

SMS-KCN cells express TRK-A receptors as well, and NGF-induced phosphorylation of $p140^{TRK-A}$ occurs. However, the downstream signaling cascade, including phosphorylation of ERK1 and ERK2 as well as induction of c-FOS and NGF1-A, was deficient. NGF also had no effect on morphological differentiation or tumor cell growth. Thus, as in some other neuroblastoma cell lines, the NGF/TRK-A signal transduction pathway in SMS-KCN cells seems to be defective, although the similar signaling BDNF/TRK-B pathway is intact. PLC-γ1 and PI-3K were weakly phosphorylated by the treatment of SMS-KCN cells with NGF. One of the explanations for this may be that there is a close association of these molecules with $p140^{TRK-A}$ near the cell membrane. It is also possible that some signaling intermediate required for immediate-early gene induction is lacking or that there is some threshold of signal transduction beyond the membrane-associated substrates that is not exceeded by NGF interacting with its receptor.

The exogenously added NT-3 induced expression of immediate-early genes in SMS-KCN cells, probably through phosphorylation of the p145$^{TRK-B}$ receptor. Although NT-3 also induced phosphorylation of p140$^{TRK-A}$, NGF was unable to induce immediate-early genes, so it is less likely that NT-3 would do so through this receptor. It is also possible that TRK-C was expressed below the level of detection or that another unknown receptor capable of binding NT-3 was responsible. However, the evidence that NT-3 could induce phosphorylation of p145$^{TRK-B}$ and the fact that BDNF can induce immediate-early gene induction make this the most plausible mechanism.

Neuroblastomas expressing TRK-A, TRK-B and/or BDNF may represent stages of the normal developmental neuronal lineage. The discovery of genes encoding neurotrophic factors and their receptors has provided considerable insight into the biology of neuroblastomas. Most primary neuroblastomas with favorable prognoses expressed a very high level of TRK-A mRNA, usually together with LNGFR mRNA. These tumor cells responded to NGF by terminally differentiating in vitro and died in the absence of NGF. These observations suggested that tumor cells expressing functional NGF receptor may be susceptible to either programmed cell death, resulting in tumor regression, or to differentiation, leading to a benign ganglioneuroma, in vivo.

Many aggressive neuroblastomas, especially those with N-myc amplification, expressed both putative full-length TRK-B and BDNF mRNAs, although generally the expression of TRK-A mRNA was extremely low or absent. The almost mutually exclusive expression of TRK-A and TRK-B (with or without BDNF) indicates that neuroblastomas may be categorized into distinct subsets. Favorable tumors are composed mainly of cells expressing TRK-A, while aggressive tumors are composed of cells expressing both TRK-B and BDNF, often accompanied by N-myc amplification.

Differential expression of TRK-A and TRK-B in neuroblastomas is consistent with the observations that neural crest-derived dorsal root ganglion cells normally require NGF and BDNF, as well as NT-3 and NT-4/5, to survive. Furthermore, TRK-A and TRK-B transcripts are observed in distinct subsets of neurons in the dorsal root ganglia and sympathetic ganglia, as seen by in situ hybridization. Finally, BDNF and/or NT-3 transcripts are present in many neurons in both dorsal root ganglia and sympathetic ganglia, whereas NGF transcripts are not. Thus, BDNF may stimulate responsive neurons by a local mechanism, and it may be particularly important in providing trophic support to sensory neurons during the earliest phases of target innervation.

We claim:

1. An isolated and pure nucleic acid molecule consisting of SEQ ID NO: 1.

2. A recombinant vector comprising SEQ ID NO: 1.

3. The recombinant vector of claim 2 wherein said recombinant vector is an expression vector and SEQ ID NO: 1 is operably linked to regulatory sequences.

4. A transformed host cell comprising a recombinant vector according to claim 3.

5. An isolated and pure nucleic acid molecule consisting of 20–150 nucleotides and further consisting of a nucleotide sequence which is identical or fully complementary to a nucleotide sequence in nucleotides 1749–3707 of SEQ ID NO: 1.

6. The nucleic acid molecule of claim 5 wherein said nucleotide sequence is identical to a nucleotide sequence in nucleotides 1749–3707 of SEQ ID NO: 1.

7. The nucleic acid molecule of claim 5 wherein said nucleotide sequence is fully complementary to a nucleotide sequence in nucleotides 1749–3707 of SEQ ID NO: 1.

8. A set of PCR primers comprising a first oligonucleotide primer and a second oligonucleotide primer, wherein said first primer and said second primer each consists of 8–20 nucleotides, and further consists of a nucleotide sequence identical or fully complementary to a nucleotide sequence of SEQ ID NO: 1, and at least one of said primers consists of a nucleotide sequence identical or fully complementary to a nucleotide sequence in nucleotides 1–158 or 1749–3707 SEQ ID NO: 1.

9. A kit for detecting human neuroblastoma having full length TRK-B protein comprising:
  a) a first container comprising a set of PCR primers according to claim 8; and
  b) a second container comprising a DNA molecule wherein said DNA molecule is equal in size to amplified cDNA produced by PCR using said primers, and wherein said cDNA is generated from an RNA transcription product of a neuro blastoma cell that expresses full length TRK-B protein.

10. A method of determining whether a human neuroblastoma cell has mRNA that encodes full length TRK-B receptor protein comprising:
  detecting the presence of an RNA molecule that encodes a full length TRK-B receptor intracellular domain by hybridizing a probe or primer to TRK-B mRNA from said neuroblastoma cell or to cDNA generated from said mRNA, wherein said probes or primers are identical or fully complementary to a sequence in nucleotides 1–158 or 1749–3707 of SEQ ID NO: 1, and detecting said hybridization.

11. The method of claim 10 wherein the presence of said RNA sequence is detected by means selected from the group consisting of:
  a) RT-PCR amplification; and
  b) oligonucleotide hybridization.

12. The method of claim 11 wherein the presence of said RNA sequence is detected by RT-PCR amplification.

13. The method of claim 12 wherein the presence of said RNA sequence is detected by PCR amplification of cDNA generated from RNA of said cell using
  PCR primers comprising a first oligonucleotide primer and a second oligonucleotide primer, wherein said first primer and said second primer each consists of 8–20 nucleotides, and further consist of a nucleotide sequence identical or fully complementary to a nucleotide sequence of SEQ ID NO: 1, and at least one of said primers consists of a nucleotide sequence identical or fully complementary to a nucleotide sequence in nucleotides 1–158 or 1749–3707 of SEQ ID NO: 1.

14. The method of claim 11 wherein the presence of said RNA sequence is detected by oligonucleotide hybridization.

15. The method of claim 14 wherein the presence of said RNA sequence is detected by oligonucleotide hybridization comprising the steps of:
  a) fixing RNA from cells to be tested to a solid phase;
  b) contacting a labeled oligonucleotide probe and said RNA, said probe consisting of 20–150 nucleotides and further consisting of a nucleotide sequence which is identical to a nucleotide sequence in nucleotides 1–158 or 1749–3707 of SEQ ID NO: 1, and
  c) detecting whether said probe hybridizes to said RNA.

16. The method of claim 14 wherein the presence of said RNA sequence is detected by oligonucleotide hybridization comprising the steps of:
  a) generating cDNA from RNA from a cell to be tested;
  b) fixing said cDNA to a solid phase;
  c) contacting a labeled oligonucleotide probe and said cDNA, said probe consisting of 20–150 nucleotides and further consisting of a nucleotide sequence which is fully complementary to a nucleotide sequence in nucleotides 1–158 or 1749–3707 of SEQ ID NO: 1; and
  d) detecting whether said probe hybridizes to said cDNA.

17. A kit for detecting mRNA that encodes full length TRK-B protein comprising:
  a) a first container containing a labeled probe consisting of 20–150 nucleotides and further consisting of a nucleotide sequence which is identical or fully complementary to a nucleotide sequence in nucleotide 1–158 or 1749–3707 of SEQ ID NO: 1; and
  b) a second container containing a DNA molecule that comprises a DNA sequence fully complementary to said probe.

18. The kit of claim 17 wherein said probe consists of a nucleotide sequence which is identical to a nucleotide sequence in nucleotides 1–158 or 1749–3707 of SEQ ID NO: 1.

19. The kit of claim 17 wherein said probe consists of a nucleotide sequence which is fully complementary to a nucleotide sequence in nucleotides 1–158 or 1749–3707 of SEQ ID NO: 1.

20. An isolated and pure nucleic acid molecule consisting of 18–28 nucleotides and further consisting of a nucleotide sequence which is identical or fully complementary to a nucleotide sequence in nucleotides 1749–3707 of SEQ ID NO: 1.

21. The nucleic acid molecule of claim 20 wherein said nucleotide sequence is identical to a nucleotide sequence in nucleotides 1749–3707 of SEQ ID NO: 1.

22. The nucleic acid molecule of claim 20 wherein said nucleotide sequence is fully complementary to a nucleotide sequence in nucleotides 1749–3707 of SEQ ID NO: 1.

* * * * *